(12) United States Patent
Peng et al.

(10) Patent No.: US 7,958,792 B2
(45) Date of Patent: Jun. 14, 2011

(54) HAND-HELD SWIPE SAMPLING DEVICE WITH SAMPLING SWAB STORAGE AND CUTTER

(75) Inventors: Hua Peng, Beijing (CN); Jianhua Liu, Beijing (CN); Wen He, Beijing (CN); Hui Li, Beijing (CN); Zhongxia Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 235 days.

(21) Appl. No.: 12/429,659

(22) Filed: Apr. 24, 2009

(65) Prior Publication Data

US 2009/0266181 A1    Oct. 29, 2009

(30) Foreign Application Priority Data

Apr. 29, 2008   (CN) .......................... 2008 1 0105508

(51) Int. Cl.
*G01N 1/04* (2006.01)
(52) U.S. Cl. .................................................. 73/864.71
(58) Field of Classification Search ............... 73/863.31, 73/864.91, 864.71; 422/104
See application file for complete search history.

(56) References Cited

U.S. PATENT DOCUMENTS

| 5,476,794 A | 12/1995 | O'Brien et al. |
| 5,571,976 A | 11/1996 | Drolet |
| 5,859,375 A * | 1/1999 | Danylewych-May et al. ........................ 73/864.71 |
| 6,321,408 B1 * | 11/2001 | Esterson et al. ............. 15/176.2 |
| 6,446,514 B1 * | 9/2002 | Danylewych-May et al. ........................ 73/863.21 |
| 6,619,143 B2 | 9/2003 | Danylewych-May et al. |
| 2002/0150513 A1 | 10/2002 | Nunes et al. |
| 2007/0137319 A1 | 6/2007 | Nacson et al. |
| 2009/0078063 A1 | 3/2009 | Zhang et al. |

FOREIGN PATENT DOCUMENTS

| CN | 2819206Y Y | 9/2006 |
| CN | 101363778 A | 2/2009 |
| WO | WO-2007/069088 A2 | 6/2007 |

OTHER PUBLICATIONS

International Search Report and Written Opinon in PCT/CN2009/000433 in Jul. 30, 2009.

* cited by examiner

*Primary Examiner* — Hezron Williams
*Assistant Examiner* — Nathaniel Kolb
(74) *Attorney, Agent, or Firm* — Marshall, Gerstein & Borun LLP

(57) ABSTRACT

The present invention relates to a hand-held swipe sampling device which can continuously supply sampling swabs. The swipe sampling device comprises a hand-held portion and a swipe sampling portion, wherein the hand grip portion is a rectangular housing in the interior of which contains a continuous sampling swab space, with a bottom cover provided on the underside of the sampling swab space, and a sampling swab outlet provided at an upper end of one side of the sampling swab space; a front end face of the swipe sampling portion configured as an accurate swipe sampling surface and provided with a sampling swab cutter. The sampling device according to the present invention is designed in a manner that continuous folded sampling swabs can be mounted and used in the sampling device such that the device can be used for many times after each mounting of the sampling swabs, thereby simplifying the mounting operations, reducing the contamination opportunities and facilitating the storage of the sampling swabs.

10 Claims, 1 Drawing Sheet

HAND-HELD SWIPE SAMPLING DEVICE WITH SAMPLING SWAB STORAGE AND CUTTER

CROSS-REFERENCE TO RELATED APPLICATIONS

This application claims the benefit of Chinese Patent Application No. 200810105508.2, filed Apr. 29, 2008.

TECHNICAL FIELD

The present invention relates to a swipe sampling device, particularly to a hand-held swipe sampling device for collecting samples from a surface of an object when an ion mobility spectrometer is used to detect explosives and drugs.

BACKGROUND ART

At present, an explosive/drug detector employing ion mobility spectrometry has become a quick, sensitive and portable instrument for field detection. The instrument has already been widely applied by military and security inspection agencies to detect the presence of trace analytes such as explosives, narcotics and chemical warfare agents, etc.

When the ion mobility spectrometer is used to detect contraband compounds, in addition to a vapor sampling mode, particle sampling is the most commonly used sampling mode. By adopting the particle sample collection mode, a sampling substrate, e.g., a sampling swab, is first used to wipe the surface of an object to collect particulates of explosives or drugs, and then the swab is inserted into the sample inlet port of the instrument for detection and identification.

Currently, particle sampling for the ion mobility spectrometer is conducted in two modes:

1. Direct Wiping

When using this mode, an operator wearing gloves holds a strip-like sampling swab as disclosed in the U.S. Pat. No. 5,476,794A or a specially shaped sampling substrate or carrier to directly wipe an article surface for sample collection. The U.S. Pat. No. 5,571,976 discloses a sample collection method using a carrier with the configuration of a small bag which can be mounted on the user's fingers. The sample carrier comprises top and bottom layers of a cotton mesh material, which are secured together along three sides, i.e., two side edges and a rear edge, and open end along a fourth side, i.e., a front edge, to enable the user's fingers to be inserted with the opening being sized to receive two fingers. Mounted on an operator's fingers, the device is run over surfaces to be tested for sample collection. It is then placed in a frame holder and inserted into an inlet port of an analysis device for analysis. To prevent the hand from contacting the surfaces of interest (the contaminated hand will interfere with the subsequent sampling and detection) or to allow for a width to accommodate the fingers, the sampling swab has to be made relatively large and correspondingly the sample feeding inlet port of the instrument is also made very large. This will not only cause great waste of sampling wipes, and, more importantly, such a very large sample inlet port has a lot of drawbacks: firstly, uncentralized heat and the resultant low heating efficiency adversely affect the sensitivity of the instrument; secondly, a large electrical power consumption shortens the working time of the battery so that the battery needs to be replaced frequently, thus affecting the application performance of the instrument.

2. Wiping Using a Sampling Device

In the mode of using a sampling device to hold a swab for swiping sampling, as disclosed in the U.S. Pat. No. 5,859,375A and the PCT patent WO2007069088A3, the hand-held sampling apparatus has a handle, a sampling head connected to the handle and a mechanism for retaining the sampling swab on the sampling head. The sampling swab is preferably a sheet-form flexible material which is mounted so as to present a collection portion thereof for sample collection. The apparatus enables quick and efficient sampling in an area to be tested, while keeping a user's hands away from the surface, and meanwhile facilitates sample collection from otherwise inaccessible areas. This imposes high requirements for the sampling apparatus. Particularly, sampling swabs are required to be flat and smooth, uncurled, unwrinkled, uncontaminated and simply operable during storage or while in use. To guarantee sampling swabs being flat and smooth, uncurled, unwrinkled and uncontaminated during storage, the sampling swabs employed by the prior art ion mobility spectrometer can only be prepared in individual pieces (single pieces). Accordingly, the swipe sampling apparatus can only be adapted for use of the individual sampling swabs, that is, for each detection a sampling swab must be taken out from a sampling swab storage container, then mounted and used for sample collection and detection. These steps not only make the sampling operations complex but, more importantly, are extremely liable to cause contamination of other unused sampling swabs which brings very serious problems for the storage of swabs.

SUMMARY OF THE INVENTION

An objective of the present invention is to overcome the drawbacks in the prior art and provide a hand-held swipe sampling device which can continuously supply sampling swabs. The device allows for multiple uses after each mounting of the sampling swabs, exhibits high sampling efficiency and keeps the sampling swabs flat uncontaminated and simply operable.

Specifically, the present invention provides a hand-held swipe sampling device, comprising: a hand grip portion and a swipe sampling portion connected together, wherein the hand grip portion is formed as a rectangular housing in the interior of which contains a sampling swab space; a bottom cover is provided on the underside of the sampling swab space; a sampling swab outlet is provided at an upper end of one side of the sampling swab space. A top surface, two side surfaces and a bottom surface of the swipe sampling portion are planar. A front end face of the swipe sampling portion is a continuous arcuate face which smoothly transits from the top surface, the two side surfaces and the bottom surface of the swipe sampling portion. The top surface of the swipe sampling portion is lower than the top surface of the rectangular housing and aligned with the sampling swab outlet. The bottom surface of the swipe sampling portion is aligned with the bottom cover. A pressing cover is provided on the top surface of the swipe sampling portion, and a cutter is disposed at the front end face of the swipe sampling portion.

Preferably, sampling swabs and/or a sampling swab box are placed in the sampling swab space.

Preferably, a locking mechanism is provided between a lower end of an end wall of the rectangular housing and the bottom cover.

Preferably, between the top surface of the rectangular housing and the pressing cover is provided a pressing cover lifting mechanism.

Preferably, a front end of the pressing cover is an arcuate face which corresponds to the front end face of the swipe sampling portion.

Preferably, the cutter has a serrated blade, and a corresponding cutter feeding slot is provided at the front end face of the sampling portion. A rod linkage unitarily connected with the cutter is provided at both ends of the cutter. The linkage is connected to a cutter drawing and rotating mechanism and a guide rail is provided at a location on both sides of the sampling portion corresponding to the linkage.

Preferably, the cutter drawing and rotating mechanism comprises a rotation shaft connected to said linkage and can be forwardly and backwardly movable and rotatable along the guide rail; the said rotation shaft is mounted on both sides of the swipe sampling portion or passes through an elongate slot-like guide rail on both sides of the sampling portion; a linkage rotation limiting stopper is provided at a lower end of said guide rail; the rotation shaft or the linkage is also connected to one end of a spring, and the other end of the spring is fixed in the swipe sampling device.

Preferably, a fixing clamp is provided on the bottom surface of the swipe sampling portion to fix the sampling swab to said continuous arcuate face.

Preferably, said fixing clamp is provided with a rotation shaft connected to a rotation shaft seat; said rotation shaft seat is provided on the side surface of the swipe sampling portion; a pressing sheet is provided on the rotation shaft to be rotatable around the rotation shaft; a magnet block is mounted in the bottom surface layer of the swipe sampling portion so that the sampling swab is tightly clamped by the force of attraction between the pressing sheet and the magnet block.

Preferably, the pressing sheet is in T-shape.

The advantages and positive effects of the hand-held swipe sampling device according to the present embodiment are as follows: since the sampling device according to the present invention is designed in a manner that continuous folded sampling swabs can be mounted and used in the sampling device to enable multiple use of the device for sampling after each mounting of the swabs, thereby simplifying the mounting operations, reducing the contamination opportunities and facilitating the storage of the sampling swabs. The swipe sampling surface is a smoothly transiting continuous curved surface so that the swab can not only be brought in full contact with the surface of the article during wiping to improve the swipe sampling efficiency, but also be prevented from deformation and wrinkles hard to restore, thereby ensuring smooth operation of sample feeding after sample collection.

BRIEF DESCRIPTION OF ACCOMPANYING DRAWINGS

In the figures, the reference number 1 designates main body; 2 swipe sampling portion; 3 pressing cover; 4 spring; 5 cutter feeding slot; 6 cutter; 7 arcuate face; 8 cutter drawing and rotating mechanism; 9 magnet block; 10 bottom cover; 11 sampling swab box; 12 fixing clamp; 13 locking mechanism; 14 sampling swab space; 15 guide rail; 16 rotation shaft; 17 sampling swab; 18 pressing cover lifting mechanism; 19 limiting stopper.

DETAILED DESCRIPTION OF PREFERRED EMBODIMENTS

The following embodiments are used to illustrate the present invention but not used to limit the scope of the present invention.

Figure 1:
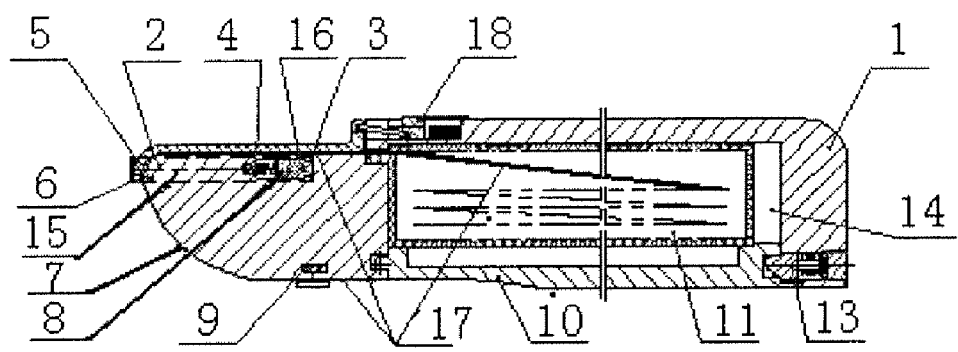
FIG. 1 is a schematic view of a hand-held swipe sampling device according to the present invention.
Figure 2:
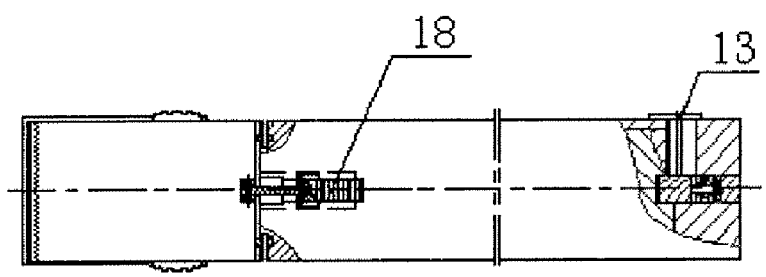
FIG. 2 is a top view of the hand-held swipe sampling device of FIG. 1.
Figure 3:
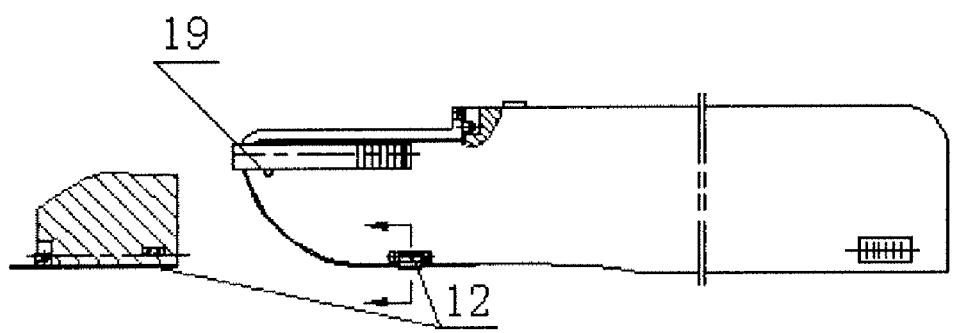
FIG. 3 is a side view of the hand-held swipe sampling device of FIG. 1.

As shown in FIGS. 1-3, according to an embodiment of the present invention, a hand-held swipe sampling device comprises a hand grip portion 1 and a swipe sampling portion 2 connected together. The hand grip portion is formed as a rectangular housing in the interior of which a sampling swab space 14 is formed. A bottom cover 10 is provided at a lower end of the sampling swab space 14. A sampling swab outlet is provided at an upper end of one side of the sampling swab space 14. A top surface, two side surfaces and a bottom surface of the swipe sampling portion 2 are planar. A front end face of the swipe sampling portion 2 is a continuous arcuate face 7 which smoothly transits from the planes of the top surface, the two side surfaces and the bottom surface of the swipe sampling portion 2 and serves as a swipe sampling surface. The top surface of the swipe sampling portion 2 is lower than the top surface of the rectangular housing and aligned with the sampling swab outlet. The bottom surface of the swipe sampling portion 2 is aligned with the bottom cover 10. On the top surface of the swipe sampling portion 2 is provided a protective pressing cover 3. A cutter 6 is disposed at the front end face of the swipe sampling portion 2.

A locking mechanism 13 is provided between the bottom cover 10 and a lower end of an end wall of the rectangular housing of the hand-held portion 1. Laminated continuous sampling swab 17 or a sampling swab storage box 111 can be placed in the sampling swab space 14 of the hand-held portion 1. Between the pressing cover 3 and the top surface of the rectangular housing is mounted a pressing cover lifting mechanism 18 which can be a hinge-like pivoting mechanism.

The sampling and wiping surface of the present invention is a smoothly transiting continuous curved surface. The swipe sampling swab 17 is provided closely against the continuous arcuate face 7, which increases a wiping and contacting area of the sampling swab 17 and a surface of an object and does not cause wrinkles and deformation affecting sample feeding.

In a preferred embodiment of the present invention, the cutter 6 is preferably mounted at an upper front end of the front end face of the swipe sampling portion 2, and preferably a serrated blade which either rotatable or backwards and forwards movable. At both ends of the cutter 6 is provided a linkage unitarily connected with the cutter, the other end of the linkage is connected to a rotation shaft 16 of a cutter drawing and rotating mechanism 8. The rotation shaft 16 is mounted in a guide rail 15 which is mounted in a groove in the side surface of the swipe sampling portion or is an elongate slot-like guide rail passing through both sides of the sampling portion. At a lower end of said guide rail is provided a linkage rotation limiting stopper 19. In the groove is mounted a spring 4 which one end is connected to the linkage of the cutter 6 or the rotation shaft and which the other end is fixed together with the side surface of the swipe sampling portion or the groove in the side surface.

A front end of the pressing cover 3 is also an arcuate face which corresponds to the arcuate face of the front end face of the swipe sampling portion 2. The functions of said pressing cover 3 with an arc include: a) to help secure the sampling swab 17; b) to protect the already drawn sampling swab 17 from contamination; c) to assist the cutter 6 in rotating onto the pressing cover 3 to facilitate the drawing and mounting of the sampling swab 17.

At the front end face of the sampling portion 2 is provided a cutter feeding channel 5 corresponding to the cutter 6. The cutter feeding channel 5 is sized and shaped to coincide with the cutter 6. The cutter 6, when not cutting the sampling swab, is configured to be located at the upper end of the pressing cover 3, and when cutting the sampling swab, is lifted and drawn forwardly, aligned with the location of the cutter feeding channel, and then pushed and pressed to sever the sampling swab, and then pulled out of the cutter feeding channel 5 and placed back on the pressing cover 3.

Specifically, both ends of the cutter 6 are connected to two linkages. The other end of the linage is connected to the rotation shaft 16, one end of the rotation shaft 16 is mounted on the guide rail 15, the guide rail is mounted in the groove of the side surface of the swipe sampling portion 2, the spring 4 is mounted on the rotation shaft or the linkage, and the other end of the spring is fixed on the side surface of the swipe sampling portion 2 or in the groove of the side surface. When the cutter 6 is drawn, the linkage and the rotation shaft connected to the cutter 6 can rotate and slide in said guide rail 15 to different positions for different operation procedures of the sampling swab such as mounting, sampling and cutting.

Preferably, a fixing clamp 12 is provided on the bottom surface of the swipe sampling portion 2 and adjacent to a rear portion of the sampling and wiping surface to fix the sampling swab 17. The fixing clamp 12 comprises a rotation shaft seat mounted on the side surface of the swipe sampling portion 2, a rotation shaft secured to the rotation shaft seat, a press sheet rotatable relative to the rotation shaft, and a magnet block 9 embedded in the swipe sampling portion 2 and working in cooperation with the rotatable press sheet, wherein the sampling swab 17 is tightly clamped by the attraction of the press sheet and the magnet block 9. Therefore, the press sheet should attract the magnet block, so it can be made from for example a ferrous metal. The fixing clamp 12 is opened away from and closed towards the sampling and wiping surface by pressing the rotatable press sheet into rotation. The rotatable pressing sheet is in T-shape.

The advantages of the hand-held swipe sampling device according to the present embodiment are as follows: since a continuous folded sampling swab can be mounted and used in the sampling device, the device can be used for many times after each time of mounting of the sampling swab, thereby simplifying the mounting operations of the sampling swab, reducing the sampling swab contaminating opportunities and facilitating the storage of the sampling swab. The sampling and wiping surface is a smoothly transiting continuous curved surface so that the sampling paper can not only be brought in full contact with the surface of the article being detected during wiping to improve the swipe sampling efficiency, but also avoid the sampling swab from deformation and wrinkles hard to restore, thereby ensuring smooth sample feeding after the sampling.

The above are preferred embodiments of the present invention. According to the disclosure of the present invention, an ordinary skill in the art can obviously conceive some identical alternative solutions which all should fall within the scope of protection of the present invention.

What is claimed:

1. A hand-held swipe sampling device, characterized in that the swipe sampling device comprises a hand-held portion (1) and a swipe sampling portion (2) connected together, wherein
    the hand-held portion (1) is formed as a rectangular housing in the interior of which a sampling swab space (14) is formed, a bottom cover (10) is provided on the underside of the sampling swab space, and a sampling swab outlet is provided at an upper end of one side of the sampling swab space (14);
    a top surface, two side surfaces and a bottom surface of the swipe sampling portion (2) are planar, a front end face of the swipe sampling portion (2) is a continuous arcuate face (7) which smoothly transits from the top surface, the two side surfaces and the bottom surface of the swipe sampling portion (2), the top surface of the swipe sampling portion (2) is lower than the top surface of the rectangular housing and flushes with the sampling swab outlet, the bottom surface of the swipe sampling portion (2) flushes with the bottom cover (10), a pressing cover (3) is provided on the top surface of the swipe sampling portion, and a cutter (6) is disposed at the front end face of the swipe sampling portion (2).

2. The hand-held swipe sampling device according to claim 1, characterized in that a sampling swab (17) and/or a sampling swab box (11) are placed in the sampling swab space (14).

3. The hand-held swipe sampling device according to claim 1, characterized in that a locking mechanism (13) is provided between a lower end of an end wall of the rectangular housing and the bottom cover (10).

4. The hand-held swipe sampling device according to claim 3, characterized in that between the top surface of the rectangular housing and the pressing cover (3) is provided a pressing cover lifting mechanism (18).

5. The hand-held swipe sampling device according to claim 4, characterized in that a front end of the pressing cover (3) is an arcuate face which corresponds to the front end face of the swipe sampling portion (2).

6. The hand-held swipe sampling device according to claim 1, characterized in that the cutter (6) is a serrated blade, at the front end face of the sampling portion (2) is provided a cutter feeding channel (5) corresponding to the cutter (6), at both ends of the cutter is provided a linkage unitarily connected with the cutter, the linkage is connected to a cutter drawing and rotating mechanism (8), and a guide rail (15) is provided at a location of both sides of the sampling portion (2) corresponding to the linkage.

7. The hand-held swipe sampling device according to claim 6, characterized in that the cutter drawing and rotating mechanism (8) comprises a rotation shaft (16) connected to said linkage and being forwardly and backwardly movable and rotatable along the guide rail (15),
    the rotation shaft (16) is mounted on both sides of the swipe sampling portion (2) or is an elongate slot-like guide rail passing through both sides of the sampling portion,
    at a lower end of said guide rail is provided a linkage rotation limiting stopper 19,
    the rotation shaft (16) or the linkage is connected to one end of a spring (4), and the other end of the spring (4) is fixed in the swipe sampling device.

8. The hand-held swipe sampling device according to claim 5, characterized in that a fixing clamp (12) is provided on the bottom surface of the swipe sampling portion (2) to fix the sampling swab (17) to said continuous arcuate face (7).

9. The hand-held swipe sampling device according to claim 8, characterized in that the fixing clamp (12) is provided with a rotation shaft connected to a rotation shaft seat, the rotation shaft seat is provided on the side surface of the swipe sampling portion (2), a press sheet is provided on the rotation shaft to be rotatable around the rotation shaft, and a magnet block (9) is mounted in the bottom surface of the swipe sampling portion (2) so that the sampling swab (17) is tightly clamped by the attraction of the press sheet and the magnet block (9).

10. The hand-held swipe sampling device according to claim 9, characterized in that the press sheet is in a T-like shape.

* * * * *